United States Patent [19]

Tresper et al.

[11] 4,070,392

[45] Jan. 24, 1978

[54] PROCESS FOR THE PRODUCTION OF O-DERIVATIVES OF P-ISOPROPENYL PHENOL

[75] Inventors: Erhard Tresper; Heinrich Krimm, both of Krefeld, Germany

[73] Assignee: Bayer Aktiengesellschaft, Germany

[21] Appl. No.: 660,243

[22] Filed: Feb. 23, 1976

[30] Foreign Application Priority Data

Feb. 27, 1975 Germany .............................. 2508512

[51] Int. Cl.$^2$ ........................ C07C 68/00; C07C 69/96
[52] U.S. Cl. ................................ 260/463; 260/669 R; 260/669 B; 260/612 D; 260/453 AR; 260/613 R; 560/130
[58] Field of Search ............... 260/669 B, 463, 669 R, 260/479 R, 612 D, 613 R, 453 AR

[56] References Cited

U.S. PATENT DOCUMENTS 2,614,080  10/1952  Welch .............................. 260/669 R

FOREIGN PATENT DOCUMENTS

| 128,013 | 7/1945 | Australia ........................ 260/669 B |
| 658,827 | 3/1963 | Canada ........................... 260/669 B |
| 903,062 | 10/1960 | United Kingdom ............. 260/669 B |

*Primary Examiner*—Delbert R. Phillips
*Attorney, Agent, or Firm*—Connolly and Hutz

[57] ABSTRACT

Process for the production of an O-derivative of p-isopropenyl phenol by splitting the corresponding O-derivative of dimeric, trimeric, oligomeric or polymeric p-isopropenyl phenol in the presence of an acid catalyst.

31 Claims, No Drawings

PROCESS FOR THE PRODUCTION OF O-DERIVATIVES OF P-ISOPROPENYL PHENOL

This invention relates to a process for the production of O-derivatives of p-isopropenyl phenol by splitting corresponding derivatives of dimeric and polymeric isopropenyl phenol.

German Auslegeschrift No. 1,193,031 relates to a process for the production of esters of p-isopropenyl phenol by reacting p-isopropenyl phenol with inorganic or organic acid chlorides or acid anhydrides. However, even when it is gently heated in the melt or in solution, especially in the presence of weakly acid and also basic catalysts, p-isopropenyl phenol changes into resin-like or crystallised oligomeric compounds, whereas in the presence of strong acids it forms a crystalline trimer. Accordingly, the known process is also carried out in the presence of inert organic solvents or water at temperatures below 50° C, preferably at temperatures below 25° C.

The hitherto known methyl and ethyl ether of p-isopropenyl phenol was not obtained by direct etherification of the phenolic hydroxyl group, but by a different method. The reaction temperature required for direct etherification is also an obstacle to the production of the ether in high yields in view of the tendency of p-isopropenyl phenol towards polymerisation.

In contrast to p-isopropenyl phenol itself, its O-derivatives are surprisingly stable and represent suitable starting and intermediate products for the production of plastics and raw materials for lacquers.

Accordingly, there is a need for a process for the production of these derivatives of p-isopropenyl phenol which avoids the disadvantages of using p-isopropenyl phenol itself and which makes it possible to obtain O-derivatives of p-isopropenyl phenol in high yields on a commercial scale.

It has now been found that an O-derivative of p-isopropenyl phenol corresponding to the formula

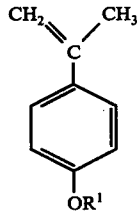

(I)

in which
R$^1$ represents an aliphatic, cycloaliphatic, araliphatic or aromatic radical which may be substituted; a cyano group; an organic or inorganic acyl radical or a halogen carbonyl, alkoxy or aroxy carbonyl radical, can be obtained by splitting the corresponding O-derivative of dimeric, trimeric, oligomeric or polymeric p-isopropenyl phenol in the presence of an acid catalyst at a temperature in the range of from 60° to 300° C.

In the context of formula I above, aliphatic radicals are straight or branched chain alkyl radicals with up to 20 carbon atoms, more preferably with up to 6 carbon atoms and more especially with up to 4 carbon atoms, the alkenyl radicals optionally containing several double bonds. Particularly suitable alkyl radicals are methyl, ethyl, propyl, isopropyl, butyl, isobutyl and tert.-butyl, also amyl and isoamyl, the other isomeric pentyl and the isomeric hexyl radicals. The following alkyl radicals are also mentioned by way of example: heptyl, octyl, nonyl, decyl, undecyl, C$_{14}$-, C$_{16}$- and C$_{18}$- radicals.

Suitable cycloalkyl radicals are those containing 5 to 12 carbon atoms, more especially cyclopentyl and cyclohexyl.

Suitable aralkyl radicals are those with up to 20 carbon atoms, more preferably with up to 12 carbon atoms, the aliphatic portion preferably containing up to 6 carbon atoms and the aromatic portion preferably 6 or 10 carbon atoms. The following are mentioned as examples of aralkyl radicals: benzyl, phenyl ethyl, phenyl propyl and phenyl isopropyl, naphthyl methyl, naphthyl ethyl, but preferably benzyl.

Suitable aryl radicals are those with 6 to 20 carbon atoms, preferably with 6 to 14 carbon atoms and more especially with 6 and 10 carbon atoms, such as for example phenyl, naphthyl, phenanthrenyl, preferably phenyl.

Where the radicals are substituted, the substituents include halogen; the hydroxy group; the nitro group; the carboxyl group (—COOH); alkyl, cycloalkyl, aralkyl and aryl radicals; alkyl carbonyl, cycloalkyl carbonyl, aralkyl carbonyl and aryl carbonyl radicals; alkoxy alkyl, aroxyalkyl, alkoxyaryl and aroxyaryl radicals, more especially phenoxyphenyl and hydroxyalkoxy, hydroxyaralkoxy and hydroxyaroxy radicals.

Suitable halogen substituents are fluorine, chlorine and bromine, preferably chlorine.

Organic and inorganic acyl radicals, halogen carbonyl, alkoxy and aroxy carbonyl radicals are preferably the groups

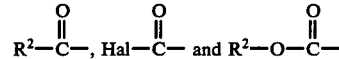

in which Hal represents halogen and R$^2$ represents an aliphatic or aromatic radical which may be substituted.

In general, the starting compounds which may be used in the process according to the invention, namely the corresponding derivatives of dimeric, trimeric, oligomeric or polymeric p-isopropenyl phenol, correspond to the tautomeric formulae

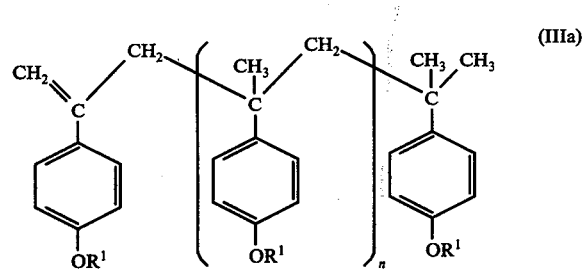

(IIIa)

and

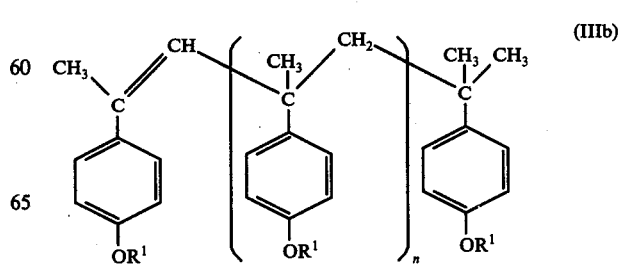

(IIIb)

in which
R¹ is as defined above and
n = 0 or an integer; n is preferably a number from 0 to 30, but more especially 0 or 1.

The starting compounds of formulae IIIa and IIIb were hitherto unknown. However, the dimer, trimer, oligomer and polymer of p-isopropenyl phenol which correspond to formula III, with the proviso that R¹ represents hydrogen, are known, for example in U.S. Pat. No. 3,288,864 and U.K. Pat. No. 903,062.

The starting compounds of formulae IIIa and IIIb, the esters and ethers of the dimers, trimers, oligomers and polymers of p-isopropenyl phenol, may be readily obtained from these compounds by known methods. Summaries of corresponding processes for the production of phenol esters and phenol ethers may be found in Houben-Weyl, Methoden der Organischen Chemie, Vol. VIII, pages 543 to 549 (1952) and Vol. VI/3, pages 49 to 90 (1965).

For example, the phenol ester may be obtained by dissolving the corresponding phenol in an excess of sodium hydroxide and slowly adding the corresponding acid chloride dropwise at room temperature without cooling, optionally in the presence of an inert water-immiscible organic solvent for the ester formed. On completion of the reaction, the organic phase is separated off and dried and the ester isolated in known manner. Corresponding esters may also be produced particularly easily by reacting the phenol with the anhydride of the corresponding acid. For example the acetic acid ester is obtained by dissolving dimeric p-isopropenyl phenol in acetic acid anhydride, slowly heating the resulting solution in the presence of catalytic quantities of an acid or tertiary amine, for example concentrated sulphuric acid or pyridine, and distilling of the acetic acid formed in a stoichiometric ratio under normal pressure. The excess acetic acid anhydride is then distilled off in a water jet vacuum, and the diacetate formed may be isolated in the usual way, for example by distillation in a high vacuum.

The ethers corresponding to formulae IIIa and IIIb may also be readily produced in known manner. For example, the methyl ether of dimeric p-isopropenyl phenol is readily obtained by adding dimethyl sulphate dropwise without cooling to a solution of the dimeric p-isopropenyl phenol in excess aqueous sodium hydroxide. After the organic phase has been separated off, washed and dried, the dimethyl ether can be isolated in the usual way by distillation in a yield of more than 90%.

Dimeric and trimeric p-isopropenyl phenol are known from U.S. Pat. No. 3,288,864 and U.K. Pat. No. 903,062.

A mixture of dimeric and oligomeric p-isopropenyl phenol may be obtained particularly easily according to German Auslegeschrift No. 1,235,849 (U.S. Pat. No. 905,994) by splitting bisphenol A and reacting the crude splitting mixture freed from phenol, which consists essentially of dimeric and oligomeric p-isopropenyl phenol, in the usual way to form the compounds of formulae IIIa and IIIb. The corresponding compounds of formulae IIIa and IIIb, in which n = 0, i.e. the dimers, may then be isolated by distillation. However, it is generally of greater advantage not to isolate the compounds, but instead to use the resulting mixture of dimeric and oligomeric compounds as starting material for the process according to the invention.

The esters of formulae IIIa and IIIb may be obtained with equal advantage by reacting the above-mentioned mixture of the dimers and oligomers of p-isopropenyl phenol, obtained by splitting bisphenol A, with acid anhydride in the presence of an acid catalyst to form the compounds of formulae IIIa and IIIb and to use the reaction product obtained directly, i.e. without separating off the acid catalyst, as starting material for the process according to the invention.

The following are mentioned as examples of the compounds corresponding to formulae IIIa and IIIb which may be used as starting material for the process according to the invention: corresponding esters of aliphatic carboxylic acids, preferably with up to 20 carbon atoms and more especially with up to 8 carbon atoms, such as the bis-acetate of dimeric p-isopropenyl phenol; the tris-acetate of trimeric p-isopropenyl phenol and O-peracetylated mixtures of monomeric, dimeric, trimeric and oligomeric p-isopropenyl phenol of the type which may be obtained in the usual way from the mixture which accumulates when bisphenol A is split by the process according to German Auslegeschrift No. 1,235,894 and the phenol separated off from the reaction mixture obtained; the propionates, butyrates, 2-ethyl hexanoates corresponding to the above-mentioned acetates; corresponding esters of aromatic carboxylic acids, such as benzoic acid; corresponding esters of chlorocarbonic acid; corresponding mixed esters of carbonic acid (carbonates) on which are based semiesters of carbonic acid with aliphatic alcohols, preferably with up to 6 carbon atoms, or phenols.

As already mentioned, the above-mentioned esters may be obtained in known manner by esterifying the phenolic hydroxyl group or groups of the corresponding monomers or oligomers of p-isopropenyl phenol.

The phenol ethers corresponding to formulae IIIa and IIIb may also be obtained by etherifying the phenolic hydroxy group or groups. The following are mentioned as examples of these phenol ethers; the alkyl ethers, preferably with up to 6 carbon atoms, more especially with up to 4 carbon atoms, such as methyl, ethyl, propyl, butyl, isopropyl, isobutyl ether and the corresponding aryl and aralkyl ethers, such as the phenyl and benzyl ethers.

Acid catalysts suitable for use in the process according to the invention include the usual acid catalysts, such as protonic and Lewis acids, natural or synthetic acid ion exchangers, acid-activated siliceous and Fuller's earths, also acid-activated molecular sieves. In general, any acid catalysts which are inert and involatile under the reaction conditions are suitable for the purpose of the process according to the invention.

This applies in particular to protonic and Lewis acids, of which only those which are involatile and which do not react with the reaction components under the reaction conditions may be used for the process according to the invention.

Accordingly, the following acids may for example be used as protonic and Lewis acids in the process according to the invention:
  mineral acids such as sulphuric acid, phosphoric acid, metaphosphoric acid and other polyphosphoric acid, boric acid, tetrafluoroboric acid;
  mineral acid salts, more especially ammonium salts and salts of the alkali metals, more especially salts of sodium and potassium, such as hydrogen sulphates, dihydrogen phosphates, acid polyphosphates;

aliphatic and aromatic carboxylic acids, preferably halogenated carboxylic acids such as fatty acids, fluorinated fatty acids, for example adipic acid;

benzoic acid, chlorobenzoic acid, terephthalic acid; aliphatic, cycloaliphatic and aromatic sulphonic acids, such as methane sulphonic acid, hexane sulphonic acid, dodecane sulphonic acid, cyclohexane sulphonic acid, benzene sulphonic acid, toluene sulphonic acid, p-chlorobenzene sulphonic acid, benzene-1,3-disulphonic acid, naphthalene sulphonic acid, naphthalene disulphonic acid;

aliphatic, cycloaliphatic, and aromatic phosphonic acids and phosphinic acids, such as cyclohexyl phosphonic acid, phenyl phosphonic acid, dimethyl phosphinic acid;

proton-acid organic compounds, such as phenols, halogenated phenols and picric acid.

The following are mentioned as examples of Lewis acids: zinc(II)chloride, tin(II)chloride, boron trifluoride, aluminium chloride, iron(III)chloride and titanium tetrachloride, copper(I)chloride, copper(II)sulphate and lithium chloride.

Suitable acid ion exchangers are natural or synthetic cation exchangers, such as zeolites or exchanger resins; exchanger resins are insoluble resins which consist of 2- or 3-dimensionally crosslinked polymers substituted by reactive groups, such as phosphoric acid, phosphonic acid, sulphuric acid or sulphonic acid groups. Particularly suitable resins are those which contain 1 sulphonic acid group per 0.5 to 2 monomer units of the resin (cf. Ullmann's Enzyklopadie der Technischen Ghemie, 3rd Edition, Vol. 8, pages 806–822 (19), especially page 816 and German Pat. No. 915,267).

It is also possible to use acid-activated siliceous and Fuller's earths, such as montmorillonites, silico-aluminates and silica gel, siliceous earths being finely divided materials which contain silica and/or aluminium oxide. These siliceous and Fuller's earths, silico-aluminates and silica gel may be activated in the usual way by treatment with acids for use as acid catalysts (cf. Chemie fur Labor und Betrieb, 1956, pages 422 to 425; Ullmanns Encyklopadie der Technischen Chemie, 3rd Edition, Vol. 4 (1953), pages 541 to 546; Vol. 9 (1957), page 271; Vol. 8 (1957), pages 801 to 804), for which purpose mineral acids such as sulphuric acid, phosphoric acid, hydrochloric acid, perchloric acid and hydrofluoric acid may be used.

Acid-activated molecular sieves may also be used as acid catalysts.

It is also possible to use mixtures of two or more acid catalysts, of which the type mentioned by way of example above, both of the same and of different groups as the acid catalyst.

The quantity of acid catalyst used in the process according to the invention may be varied within wide limits. In general, only small quantities are required, the optimum quantity being governed by the required reaction time, by the activity of the acid catalyst selected and by the reaction velocity and, hence, by the type of starting material selected and also by the type of reaction product expected. The optimum quantity of catalyst may readily be determined by a few preliminary tests.

In general, the catalyst is used in a quantity of from 0.5 to 20% by weight, preferably in a quantity of from 2 to 10% by weight and, more especially in a quantity of from 3 to b 6% by weight of the starting material.

The process according to the invention may be carried out both continuously and in batches. In cases where the process is carried out continuously, the quantity of catalyst may also be influenced by the intended residence time. In this case, it may be of advantage, also for other commercial reasons, to use a large excess of catalyst, for example when the catalyst is used in the form of a fixed-bed catalyst. In general, it is not harmful, but at the same time not recommended, to use an excess of catalyst beyond the quantity indicated above.

The reaction time may also be varied within wide limits in the process according to the invention. It can range from less than 1 second to several hours, depending on whether the reaction is carried out continuously or in batches.

In addition, the type and quantity of catalyst and starting material used can be of influence. The most favourable or necessary reaction time may readily be determined by a few preliminary tests.

In general, the process according to the invention is carried out at temperatures in the range from 60° to 300° C, preferably at temperatures in the range from 100° to 220° C and, more especially, at temperatures in the range from 120° to 180° C. It is also possible, although not generally recommended, to carry out the reaction at a lower or higher temperature. At temperatures below 60° C, the splitting process generally takes place too slowly for commercial purposes, whereas at temperatures above 300° C the yield is generally too low as a result of secondary reactions.

In general, the process according to the invention is carried out under reduced pressure, the pressure best amounting to between 0.01 and 500 Torr, preferably to between 0.05 and 50 Torr and, more especially, to between 0.1 and 20 Torr. The process may even be carried out under normal pressure. It can also be of advantage to work under normal pressure and to keep the partial pressure of the reactants within the above-mentioned range by adding a gas which is inert under the reaction conditions, such as nitrogen, helium or argon.

It can be particularly appropriate to adopt this procedure where the process according to the invention is carried out continuously.

However, the process may also be carried out in the presence of solvents and/or diluents which are inert under the reaction conditions. Dilution by inert gases, which may be particularly appropriate where the process is carried out continuously, has already been mentioned. It may also be of advantage to use solvents and/or diluents which are inert under the reaction conditions. Depending upon their boiling point, they may be used simply as diluents, for reducing the partial pressure of the reaction components or as entraining agents for the reaction product distilling off from the reaction mixture.

Suitable solvents and/or diluents are, for example, aliphatic, cycloaliphatic and aromatic hydrocarbons and chlorinated hydrocarbons, such as benzene, toluene, xylene, durol, tetralin, naphthalene, paraffin oil; aliphatic and aromatic halogenated hydrocarbons, especially chlorinated hydrocarbons, such as chlorobenzene, dichlorobenzene, chloroaphthalene; aromatic ethers such as diphenyl ether; ester of aromatic carboxylic acids, such as benzene dicarboxylic acid dimethyl and diphenyl ester.

As already mentioned, it is possible to use any conventional solvents and/or diluents which are inert under the reaction conditions. Nitrobenzene is mentioned as one example of a solvent which does not belong to any of the above-mentioned groups.

As already mentioned, however, the process according to the invention is preferably carried out in the absence of a solvent and/or diluent.

In general, the process according to the invention is carried out in batches by heating the starting material used and the catalyst used under reduced pressure until the splitting reaction commences and the monomeric reaction product begins to distil off. By correspondingly regulating the supply of heat, the temperature of the reaction mixture is regulated in such a way that the monomeric reaction product can be quickly distilled off. If the reaction and distillation rate diminishes, it may be of avantage to add more catalyst one or more times. The temperature of the reaction mixture is kept within the limits indicated above. However, it is also governed by, and varies with, the pressure selected due to the removal by distillation of the monomeric reaction product. In general, it is advisable, in cases where the process according to the invention is carried out in batches, to increase the reaction temperature to the upper limit of the above-mentioned range towards the end of the reaction in order to obtain rapid and complete distillation of the monomeric reaction product.

In order to increase yield, it can also be of advantage, even where the process according to the invention is carried out in batches, to introduce only part of the starting material together with the catalyst into the reaction zone and, corresponding to the rate at which the monomer formed distils off, to introduce the rest of the starting material either continuously or in batches into the reaction vessel. It can also be of advantage to preheat the particular quantity of starting material added to the reaction temperature.

As already mentioned, the process according to the invention may be carried out both in batches, for example in a reactor or pressure vessel, or continuously, for example in a tubular reactor. In both cases, the reaction may be carried out both in the liquid phase and in the gas phase. Where the reaction is carried out in the liquid phase, it may be sufficient to work in a two-phase system corresponding to the vapour pressure of the starting material. It is also possible, especially where the process is carried out continuously, to work in a two-phase system if, corresponding to the pressure and temperature conditions selected, not all of the starting material used can be present in the vapour phase or if the development of two phases of the starting material is intended.

Where reference is made to a two-phase system, this merely refers to the phases of the starting material used. Depending upon the type of catalyst used, it can form another, for example solid, phase. It may even form another liquid phase together with the starting material and/or reaction product.

In cases where solid catalysts are used, they may be employed in the form of fixed-bed or fluid-bed catalysts in cases where the process according to the invention is carried out continuously.

In accordance with the prior art, the process according to the invention may be carried out in a number of different ways using known apparatus.

The process according to the invention is illustrated by way of example below with reference to the formula scheme for the production of p-chloroformyloxy-α-methyl styrene from the bis-chlorocarbonic acid ester of dimeric p-isopropenyl phenol:

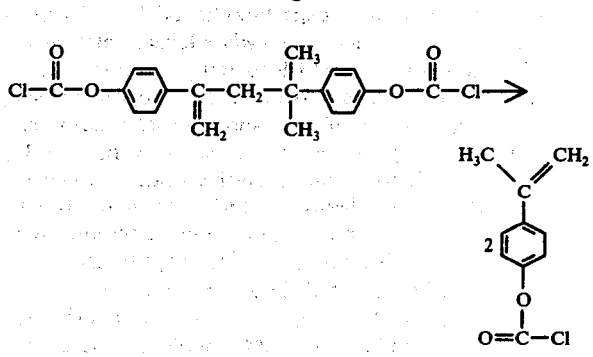

The advantage of the process according to the invention is that it overcomes the disadvantages of conventional processes. In addition, the reaction products are frequently obtained in such pure form that there is no need for further purification. However, they may be further purified in the usual way, for example by fractional distillation, recrystallisation or dissolution and crystallisation.

The compounds obtainable by the process according to the invention may be used as starting materials and intermediate products for organic syntheses. In particular, however, they are valuable monomers for the production of plastics and raw materials for lacquers.

EXAMPLE 1.1

2400 g (9 mols) p-isopropenyl phenol are dissolved under nitrogen in 2500 g (24.5 mols) of acetic acid anhydride, followed by the addition of 60 g of a standard commercial-grade acid-activated Fuller's earth. The reaction begins with a slight heat effect under which the temperature of the reaction mixture rises to about 50° C and then falls again. After the reaction temperature has fallen to around 30° C, the reaction mixture is heated very slowly until finally acetic acid distils off under normal pressure, and is maintained at that temperature until no more acetic acid distils off. The reaction mixture is then cooled and the catalyst filtered off under suction. The residual acetic acid, together with excess acetic acid anhydride, is distilled off from the filtrate in a water jet vacuum and the residue distilled in a high vacuum. The acetate of dimeric p-isopropenyl phenol is obtained in the form of a yellow oil in the boiling range from 196° to 204° C/0.2 to 0.3 Torr: yield 2506 g (81% of the theoretical).

$C_{22}H_{24}O_4$ (352.4) calculated: C 74.97%, H 6.86%; observed: C 74.40%, H 6.57%.

NMR(CDCl$_3$)ppm: 1.23(CH$_3$), 2.23(COCH$_3$), 2.80(CH$_2$), 4.81, 5.13 (=CH$_2$).

Peak area ratio: 6 : 6 : 2 : 1 : 1.

EXAMPLE 1.2

240 g (0.9 mol) of dimeric p-isopropenyl phenol are dissolved under nitrogen in 800 g of 10% by weight aqueous sodium hydroxide. 400 ml of methylene chloride are then added and the reaction mixture is cooled to 10° C. 375 g (3.6 mols) of acetic acid anhydride are added dropwise with stirring at that temperature, and the mixture subsequently stirred for another hour at 5° to 10° C. The aqueous phase is then separated off, the organic phase is washed with water, bicarbonate solution and again with water and then dried over calcined sodium sulphate. Removal of the solvent by distillation is followed by distillation in a high vacuum, giving 285 g (90% of the theoretical) of diacetate of dimeric p-isopropenyl phenol.

EXAMPLE 2.1

100 g of the diacetate of dimeric p-isopropenyl phenol are heated in vacuo with 25 g of the catalyst described in Example 1.1. The reaction begins at about 80° C and, on further heating, the reaction product distils over at 0.5 Torr in the range from 96° to 105° C. As the reaction product distils off, another 400 g (1.1 mol) of the diacetate of dimeric p-isopropenyl phenol are added dropwise, heating being regulated in such a way that the temperature of the reaction mixture guarantees continuous distillation; it is in the range from 140° to 160° C. When, towards the end of the reaction, no more reaction product distils over, the reaction mixture is cooled, another 10 g of the catalyst are added and the reaction mixture reheated until reaction product distils over again. Corresponding to distillation of the reaction product, the temperature is increased, ultimately to around 200° C, until the reaction is over and no more reaction product distils off.

The reaction product distilled off, p-isopropenyl phenol acetic acid ester, is redistilled in vacuo. It is obtained in the form of a crystal-clear liquid boiling at 83° C/0.3 Torr.

$C_{12}H_{12}O_2$ (176.2) calculated: C 74.97%, H 6.86%; observed: C 74.80%; H 6.74%.

NMR(CDCl$_3$)ppm: 2.07(CH$_3$), 2.12(COCH$_3$), 5.06,5.30(=CH$_2$),7.20(H$_{Ar}$).

Peak area ratio: 3 : 3 : 1 : 1 : 4.

EXAMPLES 2.2 TO 2.15

The following procedure was adopted for these Examples.

100 g of the diacetate of dimeric p-isopropenyl phenol are heated in vacuo with the quantity indicated in Table I below of the catalyst similarly identified in that Table. The reaction begins at about 80° C and, with further heating, the reaction product distils over at around 0.5 Torr in the range from 96° to 105° C. The temperature of the reaction mixture is regulated by corresponding heating in such a way that the reaction product continuously distils off. The temperature of the reaction mixture is between 140° and 160° C and, ultimately, rises to around 200° C until no more reaction product distils over.

The reaction product distilled off is redistilled in vacuo; it is obtained in the form of a crystal-clear liquid boiling at 83° C/0.3 Torr.

The Example number, the quantity and type of catalyst and the yield of p-isopropenyl phenol acetic acid ester (p-acetoxy-α-methyl styrene) in % of the theoretical after purification by distillation, are shown in Table I below.

Table I

| Example No. | Catalyst | Quantity (g) | p-acetoxy-α-methyl styrene (yield in % of the theoretical) |
|---|---|---|---|
| 2.2 | standard commercial-grade acid-activated Fuller's earth | 10 | 84 |
| 2.3 | phosphoric acid | 10 | 84 |
| 2.4 | sulphuric acid | 1 | 78 |
| 2.5 | polyphosphoric acid | 5 | 92 |
| 2.6 | p-toluene sulphonic acid | 5 | 86 |
| 2.7 | potassium bisulphate | 5 | 82 |
| 2.8 | standard commercial-grade strongly acid cation exchanger with sulphonic acid groups based on polystyrene | 5 | 54 |
| 2.9 | zinc chloride | 5 | 88 |
| 2.10 | aluminium trichloride | 3 | 32 |
| 2.11 | stannictetrachloride | 5 | 26 |
| 2.12 | copper sulphate | 5 | 35 |
| 2.13 | copper(I)chloride | 5 | 44 |
| 2.14 | pumice, powdered | 5 | 38 |
| 2.15 | lithium chloride | 5 | 22 |

EXAMPLE 3.1

134 g of dimeric p-isopropenyl phenol are dissolved under nitrogen in 150 g of acetic acid anhydride, followed by the addition of 7 g of the catalyst described in Example 1.1. The reaction begins with a slight heat effect under which the temperature of the reaction mixture rises to around 50° C and then falls again. When the temperature has fallen to around 30° C, the reaction mixture is heated very slowly until, finally, acetic acid distils off under normal pressure. When no more acetic acid distils over, the reaction mixture is cooled and another 5 g of catalyst are added. The remaining acetic acid and excess acetic acid anhydride are then distilled off in a water jet vacuum, and the residue heated in a high vacuum under 1.0 Torr. p-Acetoxy-α-methyl styrene distils off at a sump temperature of about 70° to 120° C, the temperature of the reaction mixture ultimately being increased to 200° C.

The reaction product obtained is redistilled; 127 g (73% of the theoretical) of p-acetoxy-α-methyl styrene are obtained in the boiling range from 79° to 81° C/0.1 Torr.

EXAMPLE 3.2

134 g of dimeric p-isopropenyl phenol are dissolved under nitrogen in 150 g of acetic acid anhydride, followed by the addition of 0.5 g of concentrated sulphuric acid. The reaction begins with a slight heat effect under which the temperature of the reaction mixture rises to around 50° C and then falls again. When the reaction temperature has fallen to around 30° C, the reaction mixture is slowly heated until, finally, acetic acid distils off under normal pressure. The temperature is regulated in such a way that distillation is continuous. When no more acetic acid distils over, the remaining acetic acid and the excess acetic acid anhydride are distilled off in a water jet vacuum, after which the reaction mixture is cooled. Another 5 g of concentrated sulphuric acid are then added, followed by heating in a high vacuum until p-acetoxy-α-methyl styrene distils off. The temperature of the reaction mixture is regulated in such a way that the reaction mixture distils off continuously; it is in the range from 70° to 120° C and is ultimately increased to 200° C. The reaction product which has distilled over is then redistilled; 119 g (68% of the theoretical) of p-acetoxy-α-methyl styrene are obtained in the boiling range from 80° to 82° C/0.1 Torr.

EXAMPLE 4.1

402 g (1.25 mols) of trimeric p-isopropenyl phenol are dissolved under nitrogen in 1500 g (14.5 mols) of acetic acid anhydride, followed by the addition of 25 g of the catalyst described in Example 1.1. The reaction begins with a slight heat effect under which the temperature of the reaction mixture rises to around 50° C and then falls again. When the temperature has fallen to around 30° C, the reaction mixture is heated very slowly until finally acetic acid distils off under normal pressure. The temperature of the reaction mixture is regulated in such a way that the acetic acid distils over continuously. When no more acetic acid distils off, the reaction mixture is cooled and the catalyst filtered off under suction. The remaining acetic acid and excess acetic acid anhydride are distilled off from the filtrate in a water jet vacuum and the residue left distilled in high vacuum. The triacetate of trimeric p-isopropenyl phenol is obtained in the form of a highly viscous oil in the boiling range from 250° to 254° C/0.3 Torr: yield 681 g (86% of the theoretical).

$C_{33}H_{36}O_6$(528.6) calculated: C 74.97%, H 6.86%; observed: C 74.60%, H 6.82%.

NMR(CDCl$_3$)ppm: 0.90, 1.42(CH$_3$), 2.17(OCH$_3$), 2.49(CH$_2$), 5.73(=CH)

Peak area ratio: 6 : 6 : 9 : 2 : 1.

EXAMPLE 4.2

100 g (0.3 mol) of the triacetate of trimeric p-isopropenyl phenol obtained in accordance with Example 4.1 are heated in vacuo with 5 g of zinc chloride. The reaction begins at about 80° C and, with further heating, the reaction product distils over at around 0.5 Torr in the range from 96° to 105° C. The temperature of the reaction mixture is regulated in such a way that the reaction product distils off continuously. It is in the range from 140° to 160° C and it is finally increased to around 200° C.

Redistillation of the reaction product distilled off gives 82 g (82% of the theoretical) of p-acetoxy-α-methyl styrene in the boiling range from 81° to 83° C/0.2 Torr.

EXAMPLE 5.1

1 kg of bisphenol A is melted under nitrogen with 5 g of powdered sodium hydroxide. Distillation is then carried out as quickly as possible in a water jet vacuum using a short column, a temperature of 130° to 150° C/15 Torr being maintained for the distillate.

935 g of distillate are thus obtained from which the phenol is distilled off in a water jet vacuum.

This leaves 512 g of a residue consisting predominantly of dimeric p-isopropenyl phenol in admixture with p-isopropenyl phenol and other oligomers of p-isopropenyl phenol.

EXAMPLE 5.2

The residue obtained in accordance with Example 5.1 is dissolved under nitrogen in 700 g of acetic acid anhydride, followed by the addition of 15 g of the catalyst described in Example 1.1. The reaction begins with a slight heat effect under which the temperature of the reaction mixture rises to around 50° C and then falls again. After the temperature has fallen to around 30° C, the reaction mixture is slowly heated until finally acetic acid distils off under normal pressure. The temperature of the reaction mixture is regulated in such a way that the acetic acid distils over continuously. When no more acetic acid distils off, the remaining acetic acid, together with excess acetic acid anhydride, is distilled off in a water jet vacuum.

EXAMPLE 5.3

Another 10 g of the catalyst are added to the reaction mixture obtained in accordance with 5.2, which contains the mixture of the acetic acid esters of the compounds obtained in accordance with 5.1, followed by heating in vacuo. The reaction begins at around 80° C and, with further heating, p-acetoxy-α-methyl styrene distils over in the range from 96° to 105° C. The sump temperature is regulated by heating in such a way that the reaction product distils off continuously; it is in the range from 140° to 160° C. When the reaction velocity and the distillation rate diminish towards the end of the reaction, the reaction mixture is cooled, another 10 g of the catalyst are added and the reaction mixture reheated until finally no more reaction product distils over, the sump temperature being increased to around 200° C.

The reaction product obtained as distillate is redistilled, giving 524 g of p-acetoxy-α-methyl styrene (74% of the theoretical, based on bisphenol A) in the boiling range from 85° to 87° C/0.35 Torr.

EXAMPLE 6.1

800 g of phosgene are dissolved in 1 liter of toluene at 5° to 10° C in a reaction vessel equipped with a gas inlet, reflux condenser and dropping funnel. To this solution is slowly added dropwise a solution of 536 g (2.5 mols) of dimeric p-isopropenyl phenol in a mixture of 535 g of N-dimethyl aniline and 1 liter of toluene. The reaction is exothermic and the reaction is cooled when the phosgene reflux becomes too vigorous. When the reaction abates, the temperature of the reaction mixture is gradually increased by heating to 60°–70° C and kept at 70° C for about 3 hours. Thereafter a clear solution has formed which is then heated to boiling point. By introducing nitrogen, the excess phosgene is removed by way of the reflux condenser. 500 ml of toluene are then distilled off from the reaction mixture under normal pressure. The reaction mixture is then cooled to room temperature and the N-dimethyl aniling hydrochloride precipitated is filtered off. The organic phase left as filtrate is washed with water and dried over calcium chloride. The toluene is then distilled off and the residue distilled in a high vacuum. 664 g (92% of the theoretical) of the bis-chlorocarbonic acid ester of dimeric p-isopropenyl phenol are obtained in the boiling range from 195° to 201° C/0.3 Torr. $C_{20}H_{18}O_4Cl_2$(393.0)calculated: C 61.07%, H 4.58%, Cl 18.07%; observed: C 61.70%, H 4.77%, Cl 17.9%.

NMR(CDCl$_3$)ppm: 1.25 (CH$_3$), 2.77 (CH$_2$), 4.88, 5.12 (=CH$_2$).

Peak area ratio: 6 : 2 : 1 : 1.

EXAMPLE 6.2

200 g of the bis-chlorocarbonic acid ester of dimeric p-isopropenyl phenol obtained in accordance with Example 6.1 are heated in vacuo with 8 g of the catalyst described in Example 1.1. The splitting reaction commences at a temperature of the reaction mixture of about 100° C and the chlorocarbonic acid ester of p-isopropenyl phenol begins to distil off. The reaction mixture is then slowly heated so that the reaction product distils over continuously, the temperature of the reaction mixture being in the range from around 140° to 150° C and finally being increased to 200° C. The reaction product distils over in the range from 82° to 90° C/0.3 Torr. The distillate obtained is then redistilled, giving 168 g (84% of the theoretical) of p-chloroformyloxy- 2methyl styrene in the boiling range from 68° to 71° C/0.1 Torr.

$C_{10}H_9O_2Cl$(196.5) calculated: C 61.07%, H 4.58%, Cl 18.07%; observed: C 61.6%, H 4.45%, Cl 18.2%.

NMR(CDCl$_3$)ppm: 2.10 (CH$_3$), 5.09, 5.32 (=CH$_2$), 7.27 (H$_{Ar}$)

Peak area ratio: 3 : 1 : 1 : 4.

EXAMPLE 7.1

134 g of dimeric p-isopropenyl phenol are melted together with 0.1 g of powdered sodium hydroxide, followed by the gradual introduction at 140° to 150° C of 44 g of ethylene oxide.

The reaction mixture is then distilled in a high vacuum, 17 g of p-(2-hydroxyethoxy)-α-methyl styrene (9% of the theoretical) distilling over as first runnings at 102° to 120° C/0.1 Torr. 147 g (83% of the theoretical) of the bis-(2-hydroxyethoxy)-derivative of dimeric p-isopropenyl phenol, in the form of a yellow oil, are obtained as the main fraction in the boiling range from 214° to 225° C/0.05 Torr.

$C_{22}H_{28}O_4$ (356.4) calculated: C 74.13%, H 7.92%; observed: C 74.0%, H 7.81%.

NMR(CDCl$_3$)ppm: 1.20(CH$_3$), 2.71(CH$_2$), 3.95(CH$_2$), 4.98, 5.08 (=CH$_2$).

Peak area ratio: 6 : 2 : 8 : 1 : 1.

EXAMPLE 7.2

100 g of the product obtained in accordance with Example 7.1 are heated in a high vacuum with 6 g of the catalyst described in Example 1.1. The reaction commences at a temperature of the reaction mixture of about 80° C and the monomeric reaction product begins to distil off. The temperature of the reaction mixture is increased in such a way that the reaction product distils off continuously. The temperature is in the range from 100° to 140° C and is only increased to 200° C towards the end of the reaction. The reaction product obtained as distillate is redistilled, in the boiling range from 104° to 106° C/0.15 Torr giving 91 g (91% of the theoretical) of 1-(2-hydroxyethoxy)-4-isopropenylbenzene melting at 78° to 80° C.

$C_{11}H_{14}O_2$ (178.2) calculated: C 74.13%, H 7.92%; observed: C 73.9%, H 7.80%.

NMR(CDCl$_3$)ppm: 2.12(CH$_3$), 2.75(OH), 4.0(CH$_2$), 5.0, 5.28(=CH$_2$), 7.12(H$_{Ar}$).

Peak area ratio: 3 : 1 : 4 : 1 : 1.

EXAMPLE 8.1

268.g (1 mol) of dimeric p-isopropenyl phenol are dissolved under nitrogen in a solution of 160 g of sodium hydroxide in 1300 ml of water. 350 g of dimethyl sulphate are added dropwise with stirring to this solution in such a way that the temperature of the solution remains in the range from 40° to 45° C. This is followed by stirring for 1 hour at 60° C. After cooling, the organic phase formed is separated off from the aqueous phase, washed with water and dried over calcium chloride. Distillation of the organic phase gives 279 g (94% of the theoretical) of the dimethyl ether of dimeric p-isopropenyl phenol in the boiling range from 149° to 152° C/0.08 Torr.

$C_{20}H_{24}O_2$ (296.4) calculated: C 81.04%, H 8.16%; observed: C 81.2%, H 8.10%.

NMR(CDCl$_3$)ppm: 1.18(CH$_3$), 2.75(OCH$_3$), 7.63(CH$_2$), 4.71, 5.08(=CH$_2$).

Peak area ratio: 6 : 6 : 2 : 1 : 1.

EXAMPLE 8.2

20 g of the dimethyl ether of dimeric p-isopropenyl phenol obtained in accordance with Example 8.1 are heated in a high vacuum together with 10 g of the catalyst described in Example 1.1 until, at about 60° C, the reaction product begins to distil off. The temperature of the reaction mixture is then regulated in such a way that the reaction product distils off continuously. The temperature of the reaction mixture is between about 60° and 83° C. When distillation of the reaction product abates or begins to stop, another 80 g of the dimethyl ether are slowly added dropwise in such a way that continuous distillation of the reaction product is guaranteed.

The distillate collected is redistilled at 78° to 80° C/3 Torr giving 52 g (52% of the theoretical) of p-isopropenyl phenyl methyl ether, in the form of a colourless distillate which solidifies on cooling (melting point 32° C).

We claim:

1. A process for the production of an O-derivative of p-isopropenyl phenol corresponding to the formula

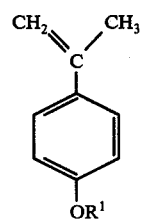

in which
R$^1$ represents an aliphatic, cycloaliphatic, araliphatic or aromatic radical which may be substituted; a cyano group; an organic or inorganic acyl radical or a halogen carbonyl or alkoxy or aroxy carbonyl radical,
which comprises heating the corresponding O-derivative of dimeric, trimeric, oligomeric or polymeric p-isopropenyl phenol at a temperature of from 60° to 300° C. in the presence of a catalytic amount of an acid catalyst which is inert and nonvolatile at the heating temperature and thereby splitting said corresponding O-derivative.

2. A process as claimed in claim 1 in which R$^1$ represents a straight or branched chain alkyl radical containing up to 20 carbon atoms.

3. A process as claimed in claim 2 in which R$^1$ represents a straight or branched chain alkyl radical containing up to 6 carbon atoms.

4. A process as claimed in claim 3 in which R$^1$ represents a straight or branched chain alkyl radical containing up to 4 carbon atoms.

5. A process as claimed in claim 1 in which R$^1$ represents an alkenyl radical.

6. A process as claimed in claim 1 in which R$^1$ represents a cycloalkyl radical which contains 5 to 12 carbon atoms.

7. A process as claimed in claim 1 in which R$^1$ represents an aralkyl radical which contains up to 20 carbon atoms.

8. A process as claimed in claim 7 in which R$^1$ represents an aralkyl radical which contains up to 12 carbon atoms.

9. A process as claimed in claim 1 in which $R^1$ represents an aryl radical which contains 6 to 20 carbon atoms.

10. A process as claimed in claim 9 in which $R^1$ represents an aryl radical which contains 6 to 14 carbon atoms.

11. A process as claimed in claim 10 in which $R^1$ represents an aryl radical which contains 6 to 10 carbon atoms.

12. A process as claimed in claim 1 in which $R^1$ represents an organic or inorganic acyl radical.

13. A process as claimed in claim 1 in which $R^1$ represents a halogen carbonyl radical.

14. A process as claimed in claim 13 in which $R^1$ represents the chlorocarbonyl radical.

15. A process as claimed in claim 1 in which $R^1$ represents an alkoxy or aroxy carbonyl radical.

16. A process as claimed in claim 1 in which the O-derivative of the dimeric, trimeric, oligomeric or polymeric p-isopropenyl phenol is a compound of one of the tautomeric formulae (IIIa)

(IIIb)

and $n$ represents 0 or any integer.

17. A process as claimed in claim 12 in which $n$ represents 0 or an integer of from 1 to 30.

18. A process as claimed in claim 13 in which $n$ represents 0 or 1.

19. A process as claimed in claim 1 in which the acid catalyst is a protonic or Lewis acid; a natural or synthetic acid ion exchanger; and acid activated siliceous or Fullers' earth or an acid activated molecular sieve.

20. A process as claimed in claim 15 in which the acid catalytst is a mineral acid or mineral acid salt; an aliphatic or aromatic carboxylic acid; an aliphatic; cycloaliphatic or aromatic sulphonic acid; an aliphatic; cycloaliphatic or aromatic phosphonic acid or a proton-acid organic compound.

21. A process as claimed in claim 15 in which the acid catalyst is zinc(II)chloride; tin(II)chloride; boron trifluoroide; aluminium chloride; iron(III)chloride; titanium tetrachloride; copper(I)chloride; copper(I)sulphate or lithium chloride.

22. A process as claimed in claim 15 in which the acid catalyst is a zeolite or exchanger resin or an acid-activated montmorillonite; a silico-aluminate; silica gel.

23. A process as claimed in claim 1 in which the acid catalyst is used in a quantity of from 0.5 to 20% by weight, based on the starting material.

24. A process as claimed in claim 19 in which the acid catalyst is used in a quantity of from 2 to 10% by weight.

25. A process as claimed in claim 20 in which the acid catalyst is used in a quantity of from 3 to 6% by weight.

26. A process as claimed in claim 22 in which the reaction is carried out at a temperature of from 100° to 220° C.

27. A process as claimed in claim 23 in which the reaction is carried out at a temperature of from 120° to 180° C.

28. A process as claimed in claim 1 in which the reaction is carried out under a pressure of from 0.01 to 500 Torr.

29. A process as claimed in claim 25 in which the reaction is carried out under a pressure of from 0.05 to 50 Torr.

30. A process as claimed in claim 1 in which the reaction is carried out under a pressure of from 0.1 to 20 Torr.

31. A process as claimed in claim 1 which is carried out in the absence of a solvent or diluent.

* * * * *